(12) United States Patent
Johnson

(10) Patent No.: US 6,918,900 B2
(45) Date of Patent: Jul. 19, 2005

(54) ABSORBENT ARTICLE WITH FRICTION-INDUCING SUBSTANCES AND METHODS FOR PREPARING SAME

(75) Inventor: Betsy Johnson, Atlanta, GA (US)

(73) Assignee: Paragon Trade Brands, Inc., Nocross, GA (US)

(*) Notice: Subject to any disclaimer, the term of this patent is extended or adjusted under 35 U.S.C. 154(b) by 0 days.

(21) Appl. No.: 09/983,809

(22) Filed: Oct. 25, 2001

(65) Prior Publication Data

US 2003/0083633 A1 May 1, 2003

(51) Int. Cl.$^7$ ................................................. A61F 13/15
(52) U.S. Cl. .................... 604/385.03; 604/387
(58) Field of Search ...................... 604/385.01, 385.03, 604/363, 386, 387, 389

(56) References Cited

U.S. PATENT DOCUMENTS

| | | | |
|---|---|---|---|
| 4,050,462 A | 9/1977 | Woon et al. | |
| 4,300,562 A | 11/1981 | Pieniak | |
| 4,946,527 A | * 8/1990 | Battrell | 156/60 |
| 5,092,861 A | 3/1992 | Nomura et al. | |
| 5,643,588 A | * 7/1997 | Roe et al. | 424/402 |
| 5,782,819 A | * 7/1998 | Tanzer et al. | 604/385.04 |
| 5,843,066 A | 12/1998 | Dobrin | |
| 5,858,013 A | 1/1999 | Kling | |
| 6,015,936 A | * 1/2000 | Takai et al. | 604/383 |
| 6,039,555 A | * 3/2000 | Tsuji et al. | 425/362 |
| 6,051,094 A | * 4/2000 | Melbye et al. | 156/269 |
| 6,135,988 A | 10/2000 | Turner et al. | |
| 6,156,818 A | 12/2000 | Corzani et al. | |
| 6,187,989 B1 | 2/2001 | Corzani et al. | |
| 6,191,189 B1 | 2/2001 | Cinelli et al. | |
| 6,213,993 B1 | 4/2001 | Zacharias et al. | |
| 6,258,076 B1 | * 7/2001 | Glaug et al. | 604/387 |
| 6,316,524 B1 | * 11/2001 | Corzani et al. | 523/111 |
| 6,478,784 B1 | * 11/2002 | Johnson et al. | 604/385.01 |

FOREIGN PATENT DOCUMENTS

| | | |
|---|---|---|
| EP | 0850618 | 7/1998 |
| EP | 0850619 | 7/1998 |
| EP | 0850620 | 7/1998 |
| EP | 0850621 | 7/1998 |
| EP | 0850622 | 7/1998 |
| EP | 0850623 | 7/1998 |
| EP | 0850624 | 7/1998 |
| EP | 0850625 | 7/1998 |
| EP | 0850626 | 7/1998 |
| EP | 0850627 | 7/1998 |
| EP | 0850628 | 7/1998 |
| WO | WO 98/23305 | 6/1998 |
| WO | WO 98/27910 | 7/1998 |
| WO | WO 98/27915 | 7/1998 |
| WO | WO 98/27916 | 7/1998 |
| WO | WO 98/27917 | 7/1998 |
| WO | WO 98/27918 | 7/1998 |
| WO | WO 98/28014 | 7/1998 |
| WO | WO 98/28016 | 7/1998 |
| WO | WO 98/28021 | 7/1998 |
| WO | WO 98/28024 | 7/1998 |
| WO | WO 00/07636 | 2/2000 |

* cited by examiner

*Primary Examiner*—Larry I. Schwartz
*Assistant Examiner*—C. Lynne Anderson
(74) *Attorney, Agent, or Firm*—Hunton & Williams LLP

(57) ABSTRACT

Absorbent articles with friction-inducing substances at one or more predetermined application zones, as well as methods for using the absorbent articles and methods for preparing the absorbent articles, are disclosed. The absorbent articles have unexpectedly superior fit, distribution, comfort, leak protection, skin protection, absorbency and/or cost-efficiency.

60 Claims, 8 Drawing Sheets

ABSORBENT ARTICLE WITH FRICTION-INDUCING SUBSTANCES AND METHODS FOR PREPARING SAME

FIELD OF THE INVENTION

The present invention relates generally to the field of absorbent articles, and more particularly to absorbent articles with friction-inducing substances, methods for using same and methods for preparing same. In particular, the present invention relates to absorbent articles having unexpectedly superior fit, distribution, comfort, leak protection, skin protection, absorbency and/or cost-efficiency, and methods for using same and methods for preparing same.

BACKGROUND OF THE INVENTION

Disposable absorbent articles typically include a moisture-impervious backing sheet, an absorbent pad, and a liner sheet that contacts the body of a person wearing the article. In addition, elasticized regions are provided around the edges of the article to secure the article about the waist and legs of a wearer. Absorbent articles, such as disposable diapers, typically further comprise opposed front and rear waist portions defining a waist opening, a crotch portion disposed there between, and a pair of elastically contractible leg openings along the side edges of the crotch portion. Disposable diapers having elasticized margins for placement about the legs of a wearer are disclosed in U.S. Pat. No. 4,050,462 and U.S. Pat. No. 5,092,861, and disposable diapers having elasticized side margins and waist band margins are disclosed in U.S. Pat. No. 4,300,562. Further, disposable diapers are conventionally fastened to the body of a user using various attachment means, including adhesive tapes, velcro tapes, spring-like clasps and flaps.

Problems with such diaper designs include shifting, shearing and conflicting movements of the article and the body of a wearer, which distort the article, and thereby cause uneven distribution of the article relative to the wearer's body and/or cause the article to move away from a position in which it is able to reliably and intimately contact the wearer's body. Such distortions cause discomfort and often result in lateral leakage of urinary or fecal material from the diaper. Further, prolonged contact of liquid or semi-solid excreta with the skin of the wearer is also aggravated under such circumstances. For example, the moisture vapor and heat generated by the bodily exudate accumulate in a pocket of the diaper, becoming trapped and then leading to conditions adjacent to a wearer's skin that promote skin irritation, infection, and the like. Although a plastic backsheet, as described above, is generally effective in precluding the passage of bodily exude outwardly, the backsheet is not efficient in preventing lateral leakage of liquids from the opposed side portions of the core sideward between the leg gathers of the backsheet and the wearer's skin. One solution to this problem, the tightening of leg gathers, presents problems in terms of the comfort of the baby and further skin irritation.

Despite previous advancements in the field of absorbent articles, persons of ordinary skill in the art continue their efforts to produce garments that fit better and thus are more comfortable and better able to contain urinary and fecal excretions. Various approaches have been attempted to improve fit and comfort of absorbent articles, while reducing lateral leakage of liquids from such articles, including the use of adhesives in such articles. In particular, direct adhesive attachment of sanitary napkins and body adhering panty shields has been disclosed. However, these approaches are all deficient in terms of effectiveness and/or cost-efficiency, as well as being limited in terms of applicability to specific types of absorbent articles, excluding diapers in particular.

For example, U.S. Pat. No. 6,213,993 B1 discloses an absorbent article having an adhesive on the bodyfacing surface for securement of the article to the wearer. The adhesive has a rheological property tan δ at 20° C. ranging from about 0.01 to about 0.6 at a frequency of about 0.1 to about 1.7 at a frequency of about 1000 radians per second. It is disclosed that, preferably, the adhesive is a hot melt adhesive.

U.S. Pat. No. 6,191,189 B1 discloses a combination of a substrate with topical adhesives for attachment to the skin. In particular the present invention relates to a combination of a substrate with a topical adhesive which can be employed for attachment to the skin in the area where absorption of bodily liquids is desired. The combination provides secure attachment and is pleasing to the skin upon application, yet causes no discomfort upon removal. This is disclosed as being achieved by selecting the chemical composition and rheological characteristics of the topical adhesives and the physical characteristics of the substrate on which the topical adhesive is applied.

U.S. Pat. No. 6,187,989 B1 discloses breathable absorbent articles particularly sanitary napkins, panty liners, adult incontinence products or sweat pads. In particular, the present invention relates to such breathable absorbent articles which are worn by direct attachment to the skin of the wearer in the area where absorption of bodily liquids is desired.

U.S. Pat. No. 6,156,818 discloses disposable absorbent articles, particularly sanitary napkins, pantiliners, adult incontinence products, or baby diapers. In particular the present invention relates to such disposable absorbent articles with side cuffs which are maintained in their in-use position by direct attachment to the skin of the wearer. The topical adhesive attachment of such side cuffs needs to be secured and pleasing upon application and during use of such articles, yet cause no discomfort upon removal of the article. This is achieved by the present invention selecting the rheological characteristics of adhesives for such articles.

U.S. Pat. No. 6,135,988 discloses an absorbent article with an adhesive flap. The absorbent article has a crotch region, a rear waist region, and a body facing surface positionable adjacent a wearer when the article is in use. The absorbent article includes a backsheet, a liquid permeable topsheet attached to the backsheet, an absorbent structure disposal between said topsheet and said backsheet, and a flap positioned in the rear waist region of the article. The flap has first and second oppositely facing major surfaces wherein the first major surface faces the top sheet and the second major surface forms a portion of the body facing surface of the absorbent article. A substantial portion of the front edge of the flap is a free edge and an adhesive is disposed on the body facing major surface of the flap whereby the adhesive may engage the skin of the wearer when the absorbent article is in use. The adhesive flap thereby prevents the formation of a gap between the absorbent article and the wearer's skin near the rear waist region and, thus inhibits the leakage of bodily exudates from the absorbent article.

EP 0 850 628 A1 discloses a tri-dimensional disposable sanitary napkin having a body facing surface and a garment facing surface, a longitudinal symmetry plane, a front end edge and a rear end edge, and comprising a liquid pervious topsheet, a backsheet joined to said topsheet and an absorbent core intermediate the backsheet and the topsheet. The absorbent core has a front portion, a central portion and a rear portion, and comprises a longitudinally oriented ridge in the central and rear portion having a profile that provides for an increased body fit. The sanitary napkin is disclosed as being intended for direct attachment to the skin of the wearer and comprises an adhesive on the body facing surface.

EP 0 850 627 A1, EP 0 850 625 A1, WO 98/27917, WO 98/27918 and WO 98/27916 disclose disposable absorbent articles capable of self shaping in use as sanitary napkins or pantiliners. In particular, the disclosures relate to such disposable absorbent articles which are worn by direct attachment to the skin of the wearer in the area were absorption of bodily liquids is desired and which are activated during use to adapt their shape to the negative three dimensional image of a wearer. The topical adhesive attachment of such articles needs to be secure and pleasing upon application and during use of such articles, yet cause no discomfort upon removal of the article. This is disclosed as being achieved by selecting the Theological characteristics of adhesives for such articles.

EP 0 850 626 A1 discloses disposable absorbent articles particularly sanitary napkins, pantiliners, adult incontinence products or sweat pads. In particular, the disclosure relates to such disposable absorbent articles which are worn by direct attachment to the skin of the wearer in the area were absorption of bodily liquids is desired. The topical adhesive attachment of such articles needs to be secure and pleasing upon application and during use of such articles, yet cause no discomfort upon removal of the article. It is disclosed that in order to provide additional comfort the articles are adaptable, and preferably elastically adaptable.

EP 0 850 624 A1, EP 0 850 622 A1, EP 0 850 619 A1 and WO 98/27910 disclose disposable absorbent articles particularly sanitary napkins, pantiliners, adult incontinence products or sweat pads. In particular, the disclosures relate to such disposable absorbent articles which are worn by direct attachment to the skin of the wearer in the area where absorption of bodily liquids is desired.

EP 0 850 623 A1 discloses disposable absorbent articles particularly sanitary napkins, pantiliners, adult incontinence products or sweat pads. In particular, the disclosure relates to such disposable absorbent articles which are worn by direct attachment to the skin of the wearer in the area were absorption of bodily liquids is desired and which articles are provided with an odor control system.

EP 0 850 621 A1 discloses disposable absorbent articles particularly sanitary napkins, pantiliners, adult incontinence products or sweat pads. In particular, the disclosure relates to such disposable absorbent articles which are worn by direct attachment to the skin of the wearer in the area were absorption of bodily liquids is desired. According to the disclosure, in order to provide the articles with additional comfort they are adaptable, and preferably elastically adaptable.

EP 0 850 620 A1 and WO 98/27915 disclose disposable absorbent articles particularly sanitary napkins, pantiliners, adult incontinence products which have side cuffs or baby diapers. In particular, the disclosures relate to such disposable absorbent articles with side cuffs which are maintained in their in use position by direct attachment to the skin of the wearer.

EP 0 850 618 A1 relates to absorbent articles capable of self shaping in use, particularly sanitary napkins or pantiliners. In particular, the disclosure relates to such disposable absorbent articles which are worn by direct attachment to the skin of the wearer in the area were absorption of bodily liquids is desired and which are activated during use to adapt to their shape to the negative three dimensional image of a wearer.

WO 00/07636 relates to disposable absorbent articles such as diapers and sanitary napkins which are provided with adhesive for attachment of the article to the skin which adhesives provide secure attachment and are pleasing to the skin upon application, yet cause no discomfort upon removal.

WO 98/28024 relates to topical adhesives for attachment to the skin. In particular, the disclosure relates to such topical adhesives which can be employed for attachment to the skin of protective articles, clothing, prosthesis, heat wraps, pads, and/or packs, e.g. for topical relief of pain or simply to provide warming; cold wraps, hearing aids, protective face masks, ornamental articles, or eye wear but excluding absorbent articles. The topical adhesives provides secure attachment and is pleasing to the skin upon application, yet causes no discomfort upon removal. This is achieved by selecting the chemical composition and rheological characteristics of the topical adhesives.

WO 98/28021, WO 98/28016 and WO 98/28014 relate to topical adhesives for attachment to the skin. In particular, the disclosures relate to such topical adhesives which can be employed for attachment to the skin of articles such as protective articles, clothing, prothesis, heat wraps, pads, and/or packs, e.g. for topical relief of pain or simply to provide warmth; cold wraps, hearing aids, protective face masks, ornamental articles or eye wear, but excluding absorbent articles, or also of functional articles such as cosmetic or pharmaceutical delivery articles that provide a substance to the skin, decorative cosmetics or cleaning articles. The topical adhesive provides secure attachment and is pleasing to the particularly the viscous modulus G" in combination with the thickness C of the topical adhesive layer in which the adhesive is provided for attachment to the skin.

WO 98/23305 relates to a polysiloxane adhesive composition that is disclosed as being useful in attaching products to human skin. It is disclosed that a disposable absorbent product may be prepared that includes the polysiloxane adhesive composition and that may be adhered directly to human skin and peeled off after use with little or no pain to the wearer.

As is apparent from the foregoing, each of the above discussed references presents a variety of means for improving fit and comfort of certain types of absorbent articles, as well as for controlling leakage in certain absorbent garments. However, all of these proposed means are deficient in terms of effectiveness and low product quality, mechanical complexity in design, specificity of application and/or associated cost inefficiencies.

In view of the deficiencies of the various products and processes disclosed in the above discussed references, it is highly desirable to provide cost-efficient absorbent articles that display superior fit, distribution, comfort, leak protection, skin protection, absorbency and/or cost-efficiency. Further, it is highly desirable to provide a cost-efficient process for producing absorbent articles having superior fit, distribution, comfort, leak protection, skin protection, absorbency and/or cost-efficiency, as well as having broad applicability.

SUMMARY OF THE INVENTION

The present invention is directed to absorbent articles, and methods for preparing and using same, that provide unexpectedly superior fit, distribution, comfort, leak protection, skin protection, absorbency and/or cost-efficiency.

An embodiment of the present invention provides absorbent articles comprising a friction-inducing substance. The friction-inducing substance is selectively located at application zones.

An embodiment of the present invention provides an absorbent article comprising: a substantially impermeable backsheet; a permeable topsheet; an absorbent core disposed between the substantially impermeable backsheet and the skin-opposing surface of said permeable topsheet; and a friction-inducing substance disposed on the skin-facing surface of the permeable topsheet at an application zone or plurality of application zones, said application zone or plurality of application zones being selectively placed to improve the fit of the absorbent article on a wearer of said absorbent article.

A further embodiment of the present invention provides an absorbent article comprising: a substantially impermeable backsheet and a permeable topsheet; said substantially impermeable backsheet and said permeable topsheet being defined by a front edge, a back edge approximately parallel to said front edge, a pair of opposing front-side application edges and a pair of opposing back-side application edges, each of said front-side and back-side application edges being disposed between and approximately perpendicular to the front edge and the back edge, and a pair of opposing leg cutout edges disposed between the pair of front-side edges and the pair of back-side edges; an absorbent core disposed between the substantially impermeable backsheet and the skin-opposing surface of said permeable topsheet; and a friction-inducing substance disposed on the skin-facing surface of the permeable topsheet at an application zone or plurality of application zones, said application zone or plurality of application zones being selectively placed to improve the fit of the absorbent article on a wearer of said absorbent article.

A still further embodiment of the present invention provides an absorbent article comprising: a substantially impermeable backsheet; a permeable topsheet having a skin-facing surface and a skin-opposing surface; said permeable topsheet being defined by a front edge, a back edge approximately parallel to said front edge, two front-side application edges and two back-side application edges, each of said front-side and back-side application edges being approximately perpendicular to the front edge and the back edge, and two leg cutout edges disposed between the two front-side edges and the two back-side edges; an absorbent core positioned between the substantially impermeable backsheet and the opposing surface of said permeable topsheet; a friction-inducing substance disposed on the skin-facing surface of said permeable topsheet at a pair of first application zones whereby the friction-inducing substance is engageable with the skin of a wearer of the absorbent article when in use, said first application zones being of a predetermined area adjacent and parallel to the front-side application edge; and a pressure-sensitive adhesive disposed on the skin-opposing surface of said substantially impermeable backsheet at a pair of second application zones, said second application zones being of a predetermined area adjacent and parallel to the back-side application edge.

An even further embodiment of the present invention provides an absorbent garment, which comprises: a front and a rear waist portion cooperating to form a waist opening, each of the front and rear waist portion being defined by a skin-facing surface and a skin-opposing surface; a crotch region formed between said front waist portion and said rear waist portion; a pair of leg cutouts on opposed sides of the crotch region; and a pair of front wing regions on the front waist portion, each of the front wing regions defining the area of the front waist portion adjacent to each said leg cutout; a pair of back wing regions on the back waist portion, each of the back wing regions defining the area of the back waist portion adjacent to each said leg cutout; a friction-inducing substance disposed on the skin-facing surface at a friction-inducing substance application zone or plurality of friction-inducing substance application zones on the each of the front wing regions, said friction-inducing substance application zone or plurality of friction-inducing substance application zones being selectively placed to improve the fit of the absorbent garment on a wearer of said absorbent garment.

Another embodiment of the present invention provides an absorbent garment, which comprises: a substantially impermeable backsheet; a permeable topsheet; an absorbent core disposed between the substantially impermeable backsheet and the skin-opposing surface of said permeable topsheet; a front and a rear waist portion cooperating to form a waist opening, each of the front and rear waist portion being defined on the skin-facing surface by the permeable topsheet and on the skin-opposing surface by the substantially impermeable backsheet; a crotch region formed between said front waist portion and said rear waist portion; a pair of leg cutouts on opposed sides of the crotch region; and a friction-inducing substance disposed on the skin-facing surface of the permeable topsheet at an application zone or plurality of application zones, said application zone or plurality of application zones being selectively placed to improve the fit of the absorbent garment on a wearer of said absorbent garment.

Yet another embodiment of the present invention is a method of preparing an absorbent article comprising: applying a friction-inducing substance to a permeable topsheet at an application zone or plurality of application zones, said application zone or plurality of application zones being selectively placed to improve the fit of the absorbent article on a wearer of said absorbent article; and forming the permeable topsheet into an absorbent article.

Still another embodiment of the present invention is a method of preparing an absorbent article comprising: applying a friction-inducing substance or a pressure sensitive adhesive to a permeable topsheet at an application zone or plurality of application zones, said application zone or plurality of application zones being selectively placed to hold each of two mechanical fasteners in a folded position during processing of said absorbent article; and forming the permeable topsheet into the absorbent article.

DETAILED DESCRIPTION OF THE INVENTION

Figure 1:
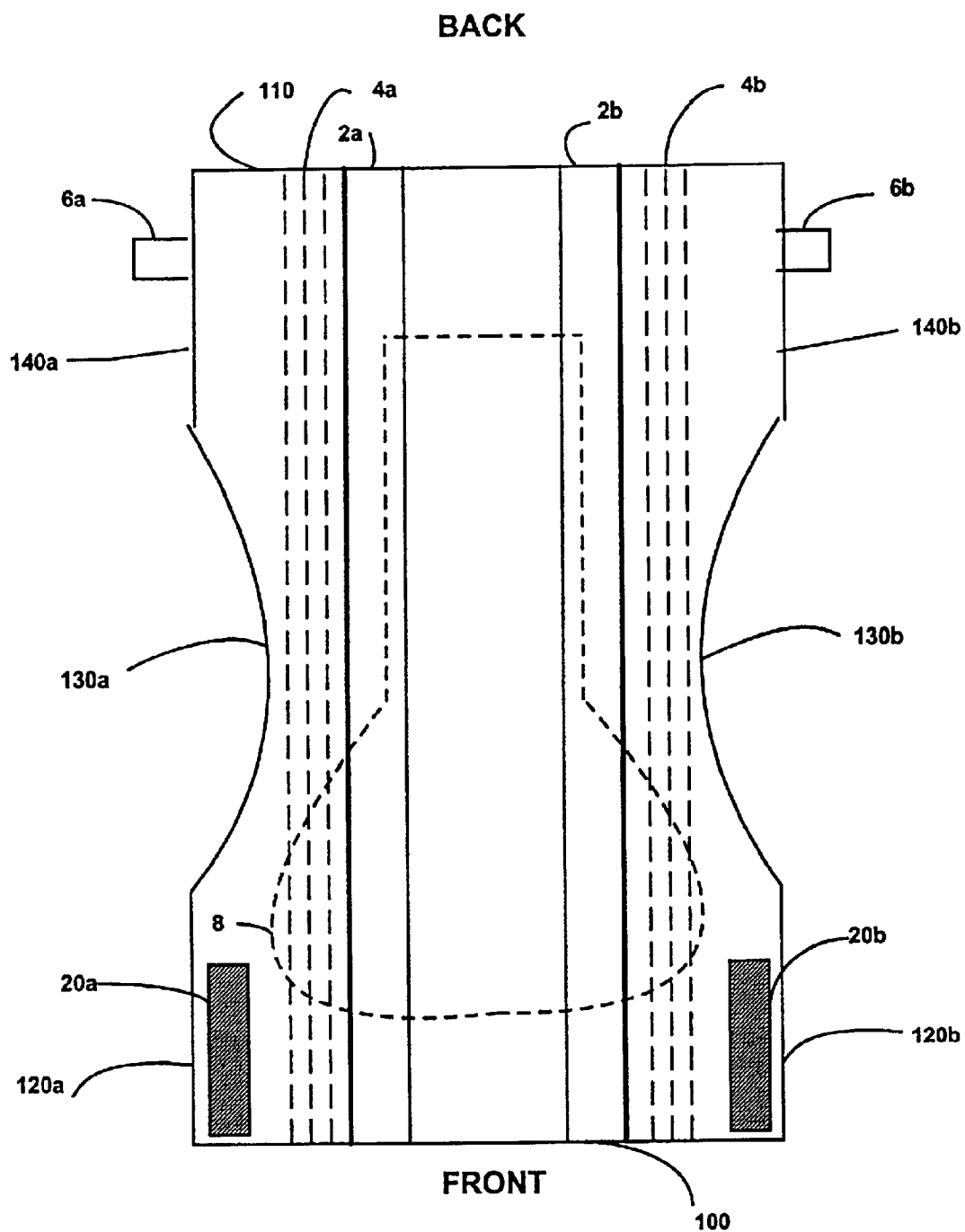
FIG. 1 is a top view of an absorbent article having a friction-inducing substance in accordance with an implementation of the present invention.

As used herein, the term "friction-inducing substance" refers to any substance that increases the coefficient of friction between at least two opposing surfaces without adhering to at least one of said opposing surfaces. The term "absorbent article," as used herein, refers to articles that absorb and contain exudates, and more specifically refers to articles which are placed against or in proximity to the body of a wearer of the absorbent article to absorb and contain various exudates discharged from the body. A non-exhaustive list of examples of absorbent articles includes diapers, diaper cores, diaper covers, disposable diapers, training pants, feminine hygiene products and adult incontinence products. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. The employance of thin, comfortable garments is disclosed, for example without limitation in U.S. Pat. No. 5,098,423 to Pineiak et al. which is herein incorporated by reference.

The present invention provides an absorbent article having unexpectedly superior properties of absorbency, leakage protection and/or skin wellness, as well as a method of preparing and a method of using the absorbent article. In particular, the present invention is directed to an absorbent article comprising: a substantially impermeable backsheet; a permeable topsheet; an absorbent core disposed between the substantially impermeable backsheet and the skin-opposing surface of said permeable topsheet; and a friction-inducing substance disposed on the skin-facing surface of the permeable topsheet at an application zone or plurality of application zones, said application zone or plurality of application zones being selectively placed to improve the fit of the absorbent article on a wearer of said absorbent article. According to an embodiment of the invention, the friction-inducing substance increases the coefficient of friction between the skin-facing surface of the permeable topsheet and the skin of the wearer when the absorbent article is in use without adhering to the skin of the wearer. The present invention can be understood by the disclosure herein and/or by reference to the drawings.

Referring to FIG. 1, an absorbent article is shown from a topsheet perspective. The absorbent article comprises a front edge 100, a back edge 110, two front-side edges 120a and 120b, two back-side edges 140a and 140b, and two leg cutout edges 130a and 130b, positioned such that leg cutout edge 130a is disposed between front-side edge 120a and back-side edge 140a, and leg cutout edge 130b is disposed between front-side edge 120b and back-side edge 140b. The absorbent article further comprises two inner leg gathers 2a and 2b, each of which extends longitudinally along the topsheet of the absorbent article from the back edge 110 to the front edge 100. The inner leg gathers 2a and 2b are approximately parallel to one another and are each positioned approximately parallel to the front-side and back-side edges 120a, 120b, 140a and 140b. Further, each inner leg gather is located adjacent to and inward of the inner most portion of the leg cutout edges 130a and 130b. A pair of front wing regions are defined as the area between each front-side edge and its adjacent inner leg gather, forward of the leg cutouts. A pair of back wing regions are defined as the area between adjacent back-side edge and its adjacent inner leg gather, rearward of the leg cutouts.

As further shown in FIG. 1, the absorbent article further comprises two leg elastics 4a and 4b, each of which is positioned approximately adjacent and parallel to each of the inner leg gathers 2a and 2b. Each of the leg elastics is located outward of said inner leg gathers 2a and 2b. Two fasteners 6a and 6b are each located at or near the back side edge of the absorbent article. An absorbent core 8 is shown as being disposed between the topsheet 40 and a substantially impermeable backsheet 50 (not shown in FIG. 1). The absorbent core 8 is positioned longitudinally along the absorbent article. Waist foam is optionally present in the absorbent article and positioned near and adjacent to the front edge 100 and/or back edge 110, on the skin-facing surface of the topsheet.

Referring still to FIG. 1, a pair of application zones 20a and 20b are shown, with a first application zone 20a being located on the topsheet adjacent to and inward of front-side edge 120a and a second application zone 20b being located on the topsheet adjacent to and inward of front-side edge 120b. Each said application zone 20a and 20b is defined as an approximately rectangular area. Each application zone 20a and 20b comprises a friction-inducing substance adhered to the permeable topsheet. The friction-inducing substance may totally or partially cover the application zone, as further described below. The illustration of the two application zones is merely illustrative. The present invention also contemplates the presence of one or more than two application zones.

Figure 2:
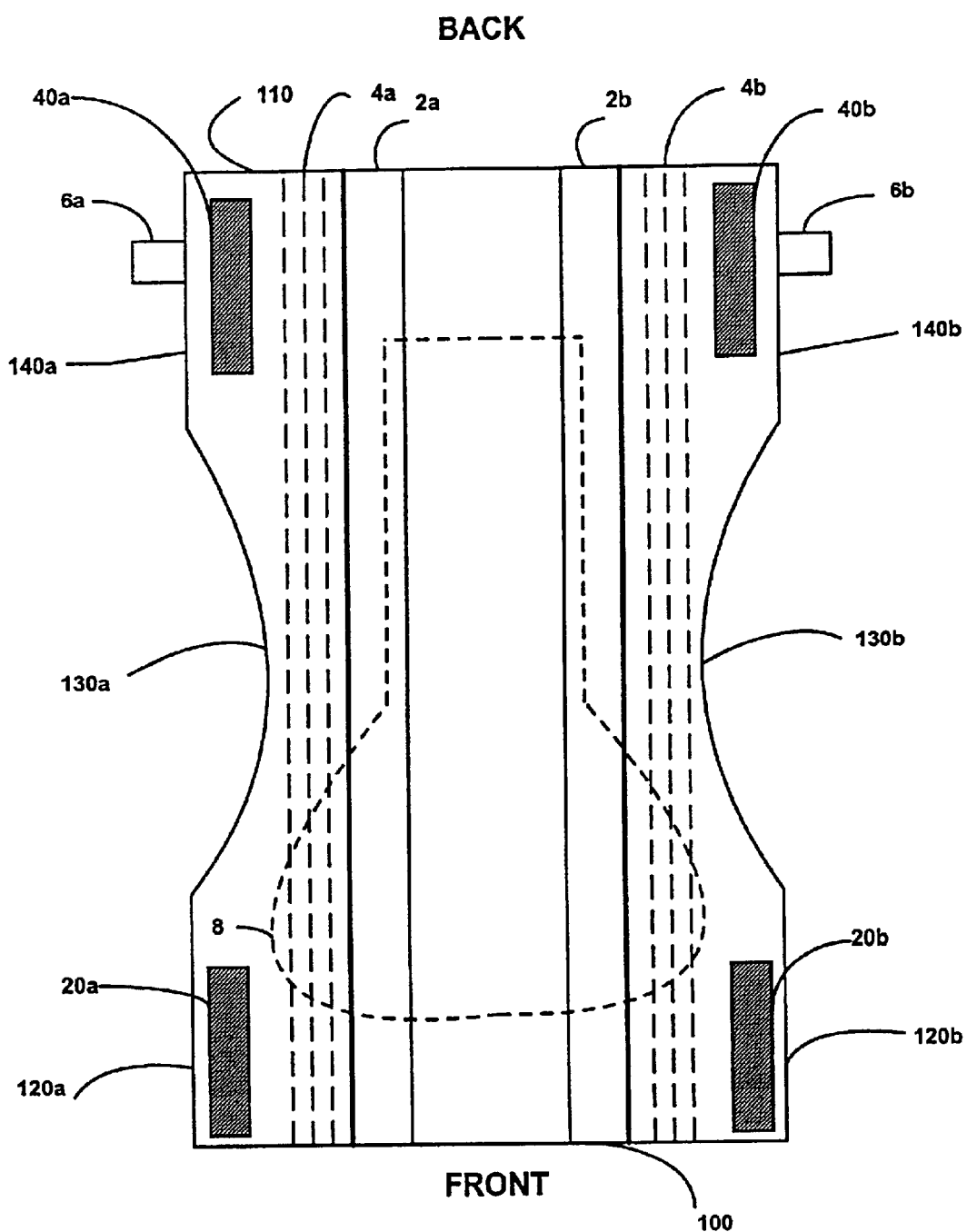
FIG. 2 is a top view of an absorbent article in accordance with an implementation of the present invention.

Referring to FIG. 2, an absorbent article is shown from a topsheet perspective. The absorbent article comprises a front edge 100, a back edge 110, two front-side edges 120a and 120b, two back-side edges 140a and 140b, and two leg cutout edges 130a and 130b, positioned such that leg cutout edge 130a is disposed between front-side edge 120a and back-side edge 140a, and leg cutout edge 130b is disposed between front-side edge 120b and back-side edge 140b. The absorbent article further comprises two inner leg gathers 2a and 2b, each of which extends longitudinally along the topsheet of the absorbent article from the back edge 110 to the front edge 100. The inner leg gathers 2a and 2b are approximately parallel to one another and are each positioned approximately parallel to the front-side and back-side edges 120a, 120b, 140a and 140b. Further, each inner leg gather is located adjacent to and inward of the inner most portion of the leg cutout edges 130a and 130b.

As further shown in FIG. 2, the absorbent article further comprises two leg elastics 4a and 4b, each of which is positioned approximately adjacent and parallel to each of the inner leg gathers 2a and 2b. Each of the leg elastics is located outward of said inner leg gathers 2a and 2b. Two fasteners 6*a* and 6*b* are each located at or near the back side edge of the absorbent article. An absorbent core 8 is shown as being disposed between the topsheet 40 and a substantially impermeable backsheet 50 (not shown in FIG. 2). The absorbent core 8 is positioned longitudinally along the absorbent article. Waist foam is optionally present in the absorbent article and positioned near and adjacent to the front edge 100 and/or back edge 110, on the skin-facing surface of the topsheet.

Referring still to FIG. 2, a pair of application zones 20*a* and 20*b* are shown, with a first application zone 20*a* being located on the topsheet adjacent to and inward of front-side edge 120*a* and a second application zone 20*b* being located on the topsheet adjacent to and inward of front-side edge 120*b*. Further, a second pair of application zones 40*a* and 40*b* are shown, with a third application zone 40*a* being located on the topsheet adjacent to and inward of back-side edge 140*a* and a fourth application zone 40*b* being located on the topsheet adjacent to and inward of back-side edge 140*b*. Each said application zone 20*a*, 20*b*, 40*a* and 40*b* is defined as an approximately rectangular area.

Figure 3:
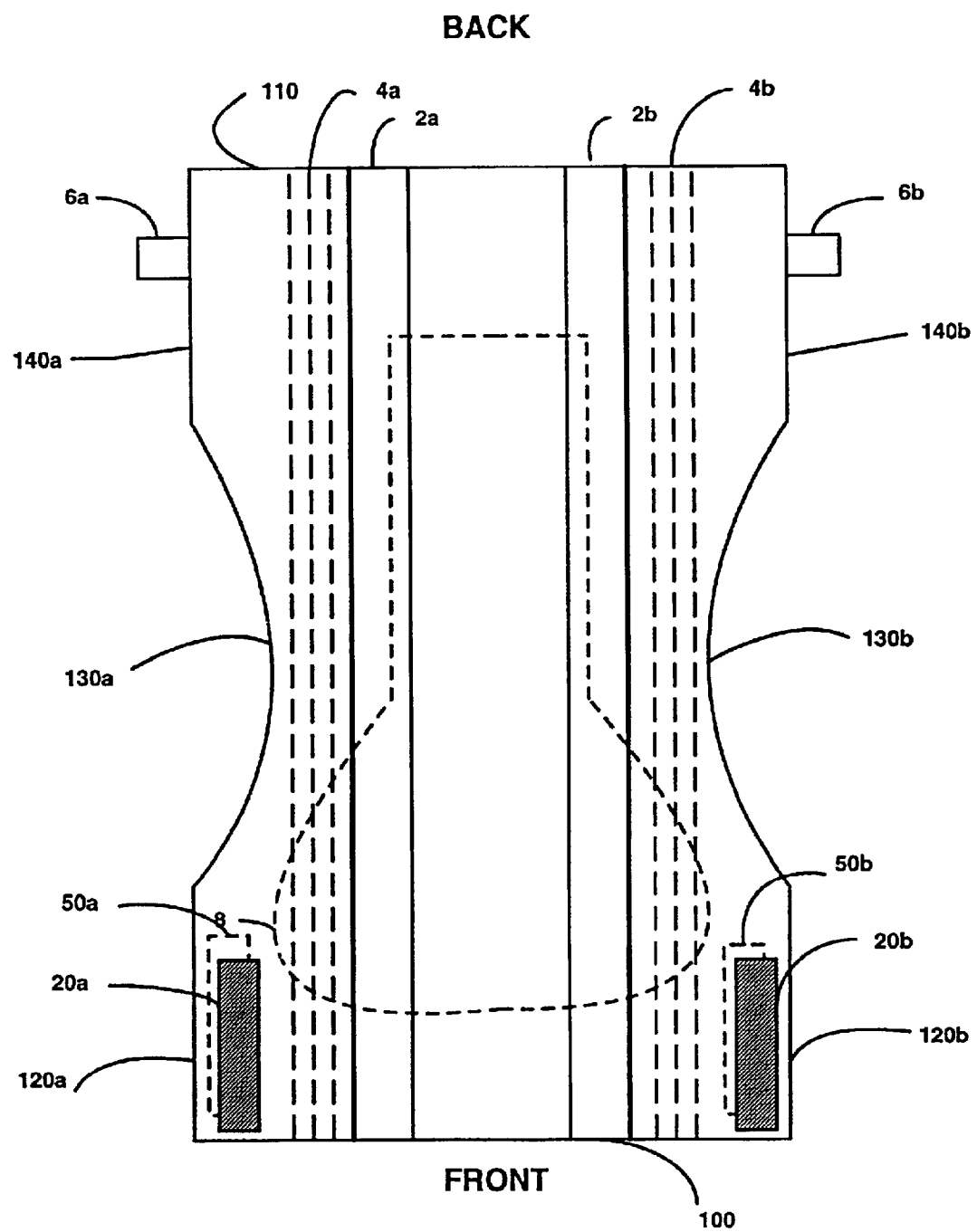
FIG. 3 is a top view of an absorbent article in accordance with an implementation of the present invention.

Referring to FIG. 3, an absorbent article is shown from a topsheet perspective. The absorbent article comprises a front edge 100, a back edge 110, two front-side edges 120*a* and 120*b*, two back-side edges 140*a* and 140*b*, and two leg cutout edges 130*a* and 130*b*, positioned such that leg cutout edge 130*a* is disposed between front-side edge 120*a* and back-side edge 140*a*, and leg cutout edge 130*b* is disposed between front-side edge 120*b* and back-side edge 140*b*. The absorbent article further comprises two inner leg gathers 2*a* and 2*b*, each of which extends longitudinally along the topsheet of the absorbent article from the back edge 110 to the front edge 100. The inner leg gathers 2*a* and 2*b* are approximately parallel to one another and are each positioned approximately parallel to the front-side and back-side edges 120*a*, 120*b*, 140*a* and 140*b*. Further, each inner leg gather is located adjacent to and inward of the inner most portion of the leg cutout edges 130*a* and 130*b*.

As further shown in FIG. 3, the absorbent article further comprises two leg elastics 4*a* and 4*b*, each of which is positioned approximately adjacent and parallel to each of the inner leg gathers 2*a* and 2*b*. Each of the leg elastics is located outward of said inner leg gathers 2*a* and 2*b*. Two fasteners 6*a* and 6*b* are each located at or near the back side edge of the absorbent article. An absorbent core 8 is shown as being disposed between the topsheet 40 and a substantially impermeable backsheet 50 (not shown in FIG. 3). The absorbent core 8 is positioned longitudinally along the absorbent article. Waist foam is optionally present in the absorbent article and positioned near and adjacent to the front edge 100 and/or back edge 110, on the skin-facing surface of the topsheet.

Referring still to FIG. 3, a pair of application zones 20*a* and 20*b* are shown, with a first application zone 20*a* being located on the skin-facing surface of the topsheet adjacent to and inward of front-side edge 120*a* and a second application zone 20*b* being located on the skin-facing surface of the topsheet adjacent to and inward of front-side edge 120*b*. A second pair of application zones 50*a* and 50*b* is also shown, with each being located on the skin-opposing surface of the backsheet corresponding to the first and second application zones 20*a* and 20*b*, respectively. Each said application zone 20*a*, 20*b*, 50*a* and 50*b* is defined as an approximately rectangular area.

Figure 4:
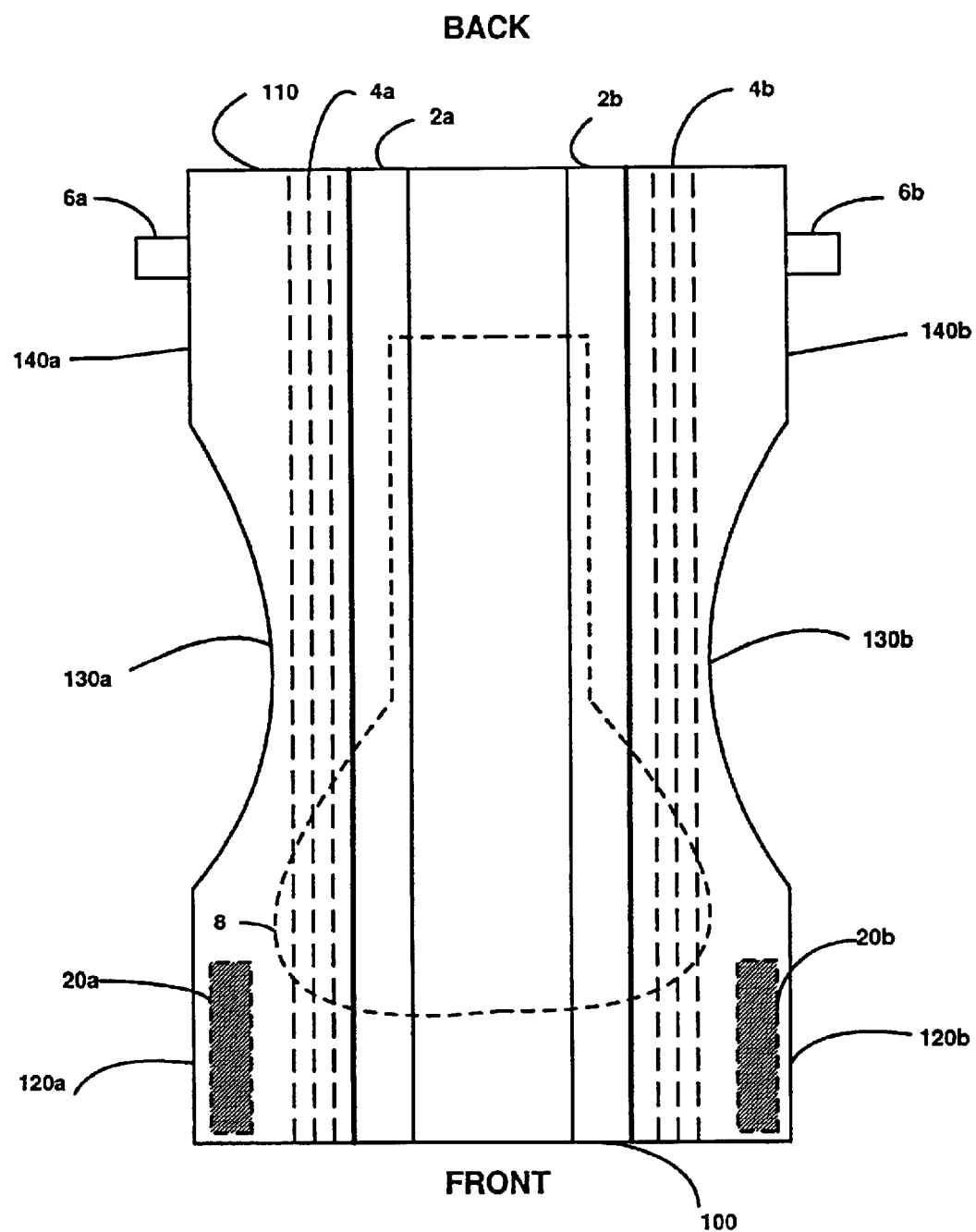
FIG. 4 is a top view of an absorbent article in accordance with an implementation of the present invention.

Referring to FIG. 4, an absorbent article is shown from a topsheet perspective. The absorbent article comprises a front edge 100, a back edge 110, two front-side edges 120*a* and 120*b*, two back-side edges 140*a* and 140*b*, and two leg cutout edges 130*a* and 130*b*, positioned such that leg cutout edge 130*a* is disposed between front-side edge 120*a* and back-side edge 140*a*, and leg cutout edge 130*b* is disposed between front-side edge 120*b* and back-side edge 140*b*. The absorbent article further comprises two inner leg gathers 2*a* and 2*b*, each of which extends longitudinally along the topsheet of the absorbent article from the back edge 110 to the front edge 100. The inner leg gathers 2*a* and 2*b* are approximately parallel to one another and are each positioned approximately parallel to the front-side and back-side edges 120*a*, 120*b*, 140*a* and 140*b*. Further, each inner leg gather is located adjacent to and inward of the inner most portion of the leg cutout edges 130*a* and 130*b*.

As further shown in FIG. 4, the absorbent article further comprises two leg elastics 4*a* and 4*b*, each of which is positioned approximately adjacent and parallel to each of the inner leg gathers 2*a* and 2*b*. Each of the leg elastics is located outward of said inner leg gathers 2*a* and 2*b*. Two fasteners 6*a* and 6*b* are each located at or near the back side edge of the absorbent article. An absorbent core 8 is shown as being disposed between the topsheet 40 and a substantially impermeable backsheet 50 (not shown in FIG. 4). The absorbent core 8 is positioned longitudinally along the absorbent article. Waist foam is optionally present in the absorbent article and positioned near and adjacent to the front edge 100 and/or back edge 110, on the skin-facing surface of the topsheet.

Referring still to FIG. 4, a pair of application zones 50*a* and 50*b* is shown, with a first application zone 50*a* being located on the skin-opposing surface of the backsheet adjacent to and inward of front-side edge 120*a* and a second application zone 50*b* being located on the skin-opposing surface of the backsheet adjacent to and inward of front-side edge 120*b*. Each said application zone 50*a* and 50*b* is defined as an approximately rectangular area. A pressure-sensitive adhesive totally or partially covers the application zone as described below.

Figure 5:
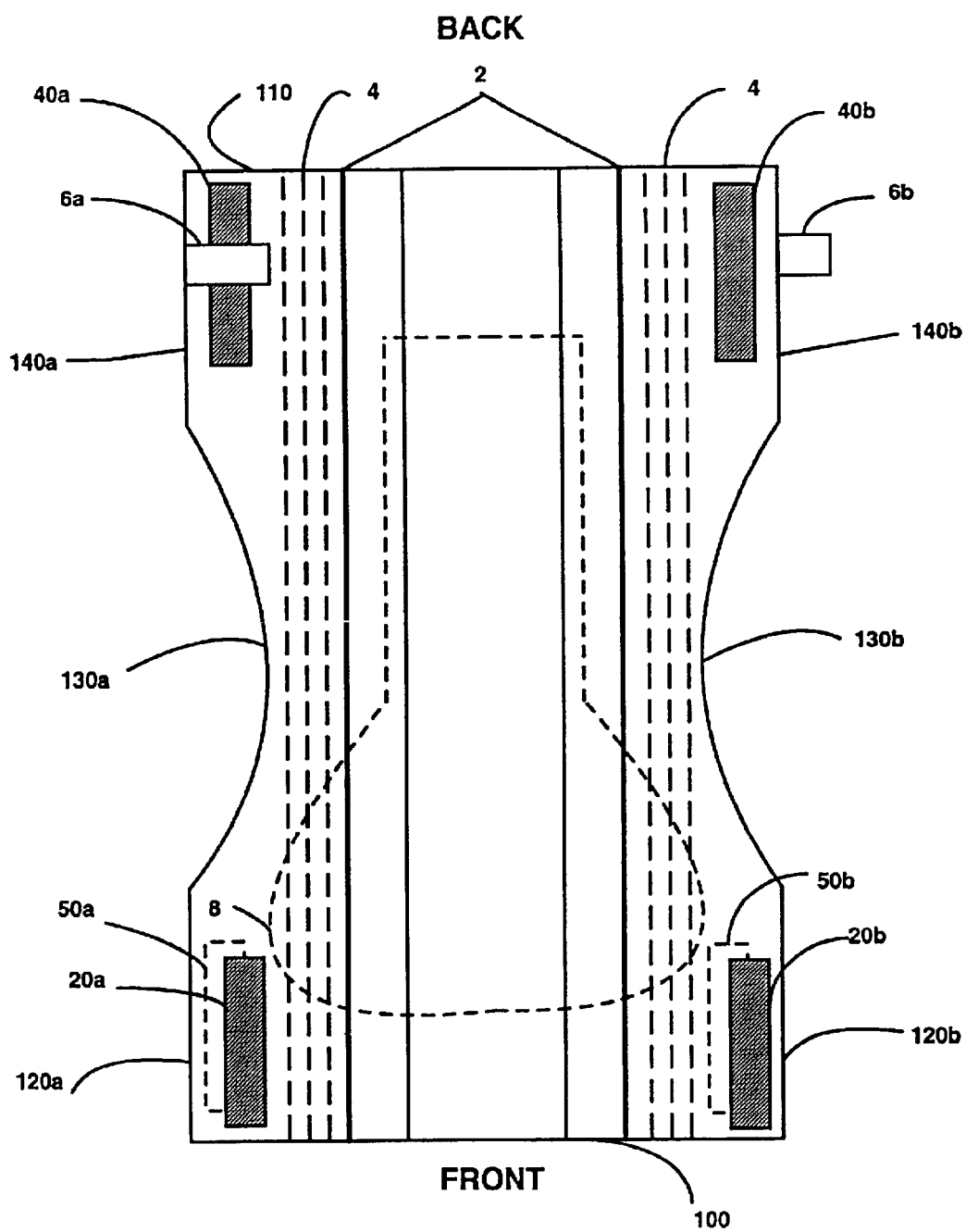
FIG. 5 is a top view of an absorbent article in accordance with an implementation of the present invention.

Referring to FIG. 5, an absorbent article is shown from a topsheet perspective. The absorbent article comprises a front edge 100, a back edge 110, two front-side edges 120*a* and 120*b*, two back-side edges 140*a* and 140*b*, and two leg cutout edges 130*a* and 130*b*, positioned such that leg cutout edge 130*a* is disposed between front-side edge 120*a* and back-side edge 140*a*, and leg cutout edge 130*b* is disposed between front-side edge 120*b* and back-side edge 140*b*. The absorbent article further comprises two inner leg gathers 2*a* and 2*b*, each of which extends longitudinally along the topsheet of the absorbent article from the back edge 110 to the front edge 100. The inner leg gathers 2*a* and 2*b* are approximately parallel to one another and are each positioned approximately parallel to the front-side and back-side edges 120*a*, 120*b*, 140*a* and 140*b*. Further, each inner leg gather is located adjacent to and inward of the inner most portion of the leg cutout edges 130*a* and 130*b*.

As further shown in FIG. 5, the absorbent article further comprises two leg elastics 4*a* and 4*b*, each of which is positioned approximately adjacent and parallel to each of the inner leg gathers 2*a* and 2*b*. Each of the leg elastics is located outward of said inner leg gathers 2*a* and 2*b*. Two fasteners 6*a* and 6*b* are each located at or near the back side edge of the absorbent article. An absorbent core 8 is shown as being disposed between the topsheet 40 and a substantially impermeable backsheet 50 (not shown in FIG. 5). The absorbent core 8 is positioned longitudinally along the absorbent article. Waist foam is optionally present in the absorbent article and positioned near and adjacent to the front edge 100 and/or back edge 110, on the skin-facing surface of the topsheet.

Referring still to FIG. 5, a pair of application zones 20a and 20b are shown, with a first application zone 20a being located on the topsheet adjacent to and inward of front-side edge 120a and a second application zone 20b being located on the topsheet adjacent to and inward of front-side edge 120b. Further, a second pair of application zones 40a and 40b are shown, with a third application zone 40a being located on the topsheet adjacent to and inward of back-side edge 140a and a fourth application zone 40b being located on the topsheet adjacent to and inward of back-side edge 140b. Additionally, a third pair of application zones 50a and 50b is shown, with a fifth application zone 50a being located on the skin-opposing surface of the backsheet adjacent to and inward of front-side edge 120a and a sixth application zone 50b being located on the skin-opposing surface of the backsheet adjacent to and inward of front-side edge 120b. Each said application zone 20a, 20b, 40a, 40b, 50a and 50b is defined as an approximately rectangular area.

Also shown in FIG. 5 is an absorbent article having a pair of mechanical fasteners 6a and 6b. In accordance with an implementation of the present invention, each of a pair of mechanical fasteners 6a and 6b is held in the folded position (e.g., as shown for mechanical fastener 6a in FIG. 5, as compared to mechanical fastener 6b which is not shown as folded in FIG. 5) during processing by the friction-inducing substance and/or pressure sensitive adhesive at the application zones. In this manner, unexpectedly superior cost efficiency in the processing of absorbent articles in accordance with an implementation of the present invention is achieved.

Figure 6:
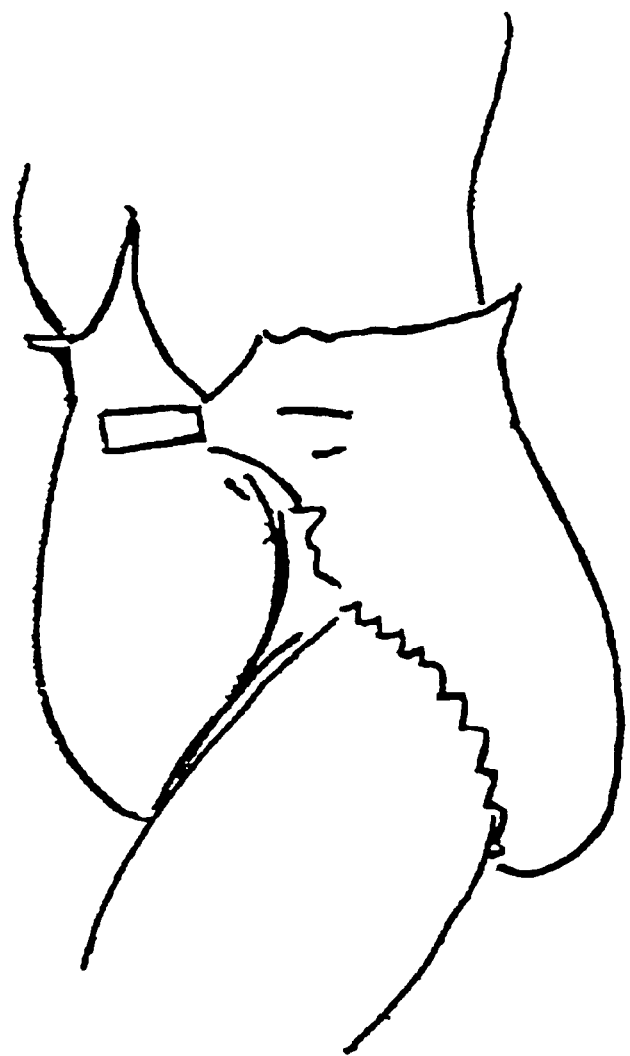
FIG. 6 is a side view illustration showing the sagging of a conventional diaper during use.

Referring to FIG. 6, a side view illustration shows the sagging of a conventional diaper during use. The sagging represents uneven distribution of the diaper around the body of the wearer. This uneven distribution is accompanied by discomfort to the wearer and leakage of fluid.

Figure 7:
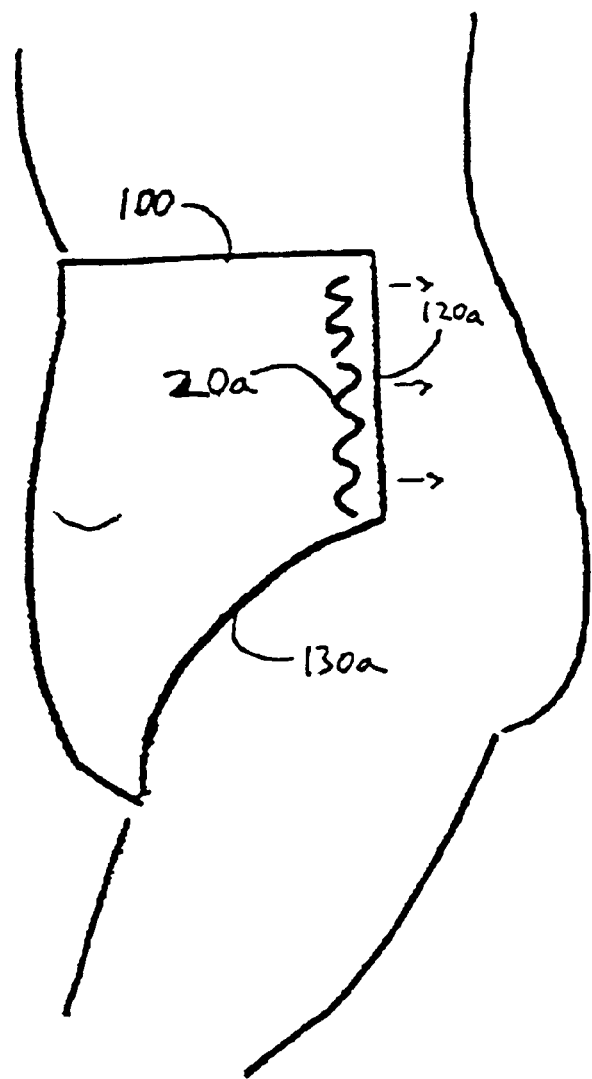
FIG. 7 is a side view illustration showing the selective placement of a friction-inducing substance at an application zone in accordance with an implementation of the present invention.

Referring to FIG. 7, a side view illustration shows the selective placement of a friction-inducing substance at an application zone in accordance with an implementation of the present invention. As shown, the friction-inducing substance on the non-tape end of the diaper holds the front wing area of the diaper against the skin. Friction keeps tension on the front waist band. In this manner, the forces are distributed more evenly for a snug fit to the body of the wearer.

Figure 8:
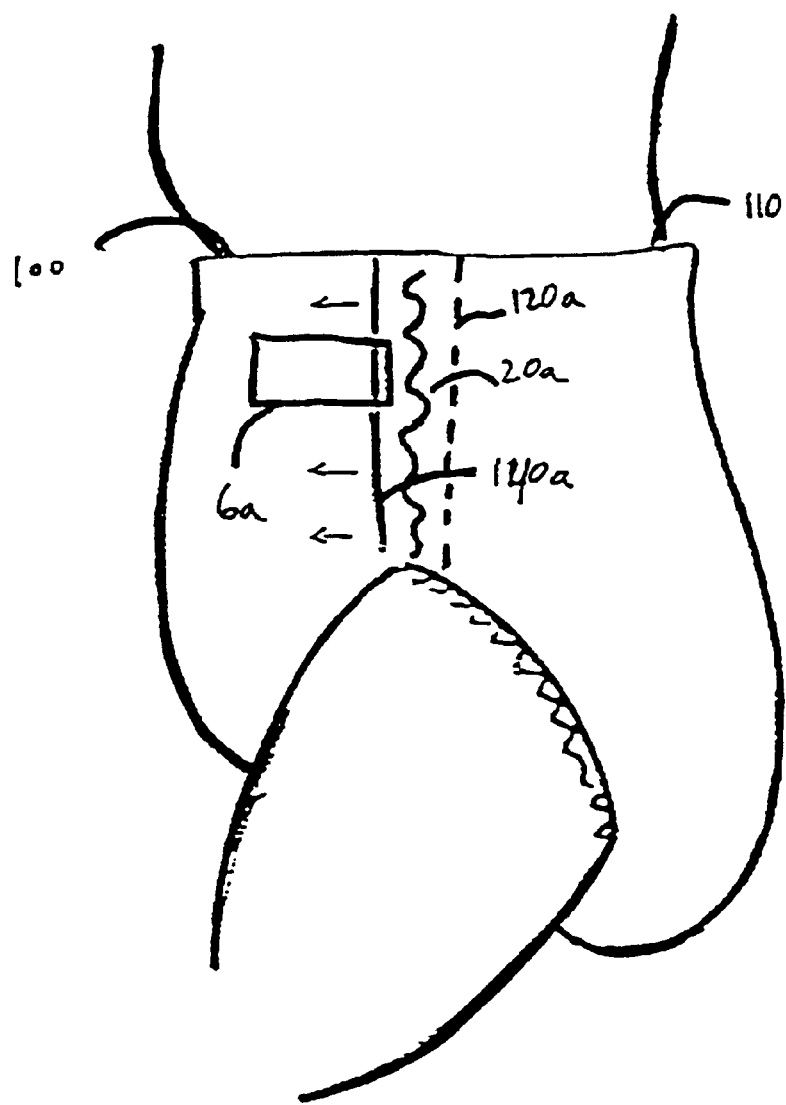
FIG. 8 is a side view comparative illustration showing the uniform distribution about a wearer of a diaper in accordance with an implementation of the present invention.

Referring to FIG. 8, a side view comparative illustration shows the uniform or even distribution about a wearer of a diaper in accordance with an implementation of the present invention, for example, as in FIG. 7. The uniform or even distribution of the diaper about the wearer as shown in FIG. 8 results in substantially less sagging than the diaper shown in FIG. 6. Accordingly, it should be readily apparent that the elimination or minimization of such sagging represents a substantial improvement in terms of fit, comfort and leakage protection for the wearer of the diaper.

The friction-inducing substance at each of the application zones adjacent the front-side edges of the skin-facing surface of the permeable topsheet is engageable with the skin of a wearer of the absorbent article when the article is in use. The friction-inducing substance is optionally disposed on the skin-facing surface of the permeable topsheet at two application zones.

The friction-inducing substance increases the coefficient of friction between the skin-facing surface of the permeable topsheet and the skin of the wearer when the absorbent article is in use without adhering to the skin of the wearer. Preferably, the friction-inducing substance increases the coefficient of friction between the permeable topsheet of the absorbent article and the skin of a wearer of the absorbent article by about 25% to about 500% when the absorbent article is in use. More preferably, the friction-inducing substance increases the coefficient of friction between the permeable topsheet of the absorbent article and the skin of a wearer of the absorbent article by about 50% to about 200% when the absorbent article is in use. Even more preferably, the friction-inducing substance increases the coefficient of friction between the permeable topsheet of the absorbent article and the skin of a wearer of the absorbent article by about 60% to about 140% when the absorbent article is in use. Most preferably, the friction-inducing substance increases the coefficient of friction between the permeable topsheet of the absorbent article and the skin of a wearer of the absorbent article by about 80% to about 100% when the absorbent article is in use.

Any effective friction-inducing substance may be used in implementing the present invention. Acceptable friction-inducing substances include organic and inorganic substances. Acceptable organic substances include natural and synthetic substances. Preferably, the friction-inducing substance is selected from the group consisting of rubber-solvents, cellulosics, gums, minerals, polymers, resins and combinations thereof. More preferably, the friction-inducing substance is selected from the group consisting of polymers and combinations thereof. Even more preferably, the friction-inducing substance is Product No. 10958-17-1 available from National Starch and Chemical, Inc. located in Bridgewater, N.J. Persons of ordinary skill in the art are readily able to identify, select and utilize friction-inducing substances to implement the present invention, based upon the guidance provided herein.

The friction-inducing substance is optionally a skin-friendly substance. A skin-friendly substance is any substance that is not generally harmful to skin upon contact and/or is beneficial, or generally perceived as being beneficial, to skin upon contact. Skin-friendly substances are well known in the art. Persons of ordinary skill in the art would be readily capable of selecting and incorporating such skin-friendly substances in accordance with implementing the present invention, based upon the guidance provided herein.

The absorbent article may additionally comprise a pressure-sensitive adhesive. Any effective pressure-sensitive adhesive may be used in implementing the present invention. Acceptable pressure-sensitive adhesives include organic and inorganic substances. Acceptable organic substances include natural and synthetic substances. Persons of ordinary skill in the art are readily able to identify, select and utilize friction-inducing substances to implement the present invention, based upon the guidance provided herein.

The pressure-sensitive adhesive is preferably disposed on the skin-facing surface of the permeable topsheet at two application zones, each said application zone being defined by a predetermined area adjacent to and approximately parallel to each of a pair of back-side application edges. More preferably, a pressure-sensitive adhesive is disposed on the skin-facing surface of the permeable topsheet at four application zones, each said application zone being defined by a predetermined area adjacent to and approximately parallel to each of the two front-side application edges and each of the two back-side application edges. The pressure-sensitive adhesive is preferably engageable with the skin-opposing surface of the substantially impermeable backsheet at a receiving zone.

The absorbent article of the present invention is substantially evenly distributed around the body of the wearer during use, according to an implementation of the present invention. Even distribution of the absorbent article is enabled through the selectively placed friction-inducing substance, and the optional selectively placed pressure-sensitive adhesive. The even distribution improves fit and comfort of the absorbent article and consequently provides unexpectedly superior leakage protection.

The friction-inducing substance may be disposed on the skin-facing surface of the permeable topsheet at two application zones, each said application zone being defined by a predetermined area adjacent to and approximately parallel to each of the two front-side application edges or each of the two back-side application edges. Preferably, the friction-inducing substance is disposed on the skin-opposing surface of the substantially impermeable backsheet at two application zones, each said application zone being defined by a predetermined area adjacent to and approximately parallel to each of the two front-side application edges or each of the two back-side application edges. Even more preferably, the friction-inducing substance is disposed on the skin-facing surface of the permeable topsheet at the two application zones, wherein the two application zones on the skin-facing surface of the permeable topsheet are defined by a predetermined area adjacent to and approximately parallel to each of the two front-side application edges; and wherein the two application zones on the skin-opposing surface of the permeable are defined by a predetermined area adjacent to and approximately parallel to each of the two front-side application edges or each of the two back-side application edges.

Each application zone is located a distance from the front-side and/or back-side edges of the topsheet that is effective in providing superior fit, comfort and leakage protection, as well as other superior characteristics. Preferably, the outmost portion of each application zone is about 0.1 mm to about 190 mm from said front-side application edge or said back-side application edge. More preferably, the outmost portion of each application zone is about 5 mm to about 50 mm from said front-side application edge or said back-side application edge. Even more preferably, the forward-most portion of each application zone adjacent to the front-side edge is about 0 mm to about 200 mm from the front edge of the permeable topsheet. Most preferably, the forward-most portion of each application zone adjacent to the front-side edge is about 0 mm to about 100 mm from the front edge of the permeable topsheet.

Each application zone optionally forms a substantially rectangular area. Preferably, the substantially rectangular area is about 2 mm to about 190 mm in width and about 5 mm to about 200 mm in length. More preferably, the substantially rectangular area of about 5 mm to about 60 mm in width and about 10 mm to about 100 mm in length.

The friction-inducing substance totally or partially covers the application zone. When the friction-inducing substance partially covers the application zone the friction-inducing substance may form a pattern thereon. Preferably, the pattern is selected from the group consisting of spiral, random fiberization, zoned slot and combinations thereof. The use of such a pattern may provide cost efficiency. Further, the friction-inducing substance is preferably of a substantially uniform application density.

According to an implementation of the present invention, an absorbent article comprises: a substantially impermeable backsheet and a permeable topsheet; said substantially impermeable backsheet and said permeable topsheet being defined by a front edge, a back edge approximately parallel to said front edge, a pair of opposing front-side application edges and a pair of opposing back-side application edges, each of said front-side and back-side application edges being disposed between and approximately perpendicular to the front edge and the back edge, and a pair of opposing leg cutout edges disposed between the pair of front-side edges and the pair of back-side edges; an absorbent core disposed between the substantially impermeable backsheet and the skin-opposing surface of said permeable topsheet; and a friction-inducing substance disposed on the skin-facing surface of the permeable topsheet at an application zone or plurality of application zones, said application zone or plurality of application zones being selectively placed to improve the fit of the absorbent article on a wearer of said absorbent article.

According to another implementation of the present invention, an absorbent article comprises: a substantially impermeable backsheet; a permeable topsheet having a skin-facing surface and a skin-opposing surface; said permeable topsheet being defined by a front edge, a back edge approximately parallel to said front edge, two front-side application edges and two back-side application edges, each of said front-side and back-side application edges being approximately perpendicular to the front edge and the back edge, and two leg cutout edges disposed between the two front-side edges and the two back-side edges; an absorbent core positioned between the substantially impermeable backsheet and the opposing surface of said permeable topsheet; a friction-inducing substance disposed on the skin-facing surface of said permeable topsheet at a pair of first application zones whereby the friction-inducing substance is engageable with the skin of a wearer of the absorbent article when in use, said first application zones being of a predetermined area adjacent and parallel to the front-side application edge; and a pressure-sensitive adhesive disposed on the skin-opposing surface of said substantially impermeable backsheet at a pair of second application zones, said second application zones being of a predetermined area adjacent and parallel to the back-side application edge.

Due to the wide variety of materials which may be incorporated into the absorbent articles of the present invention, the present invention is not intended to be limited to any specific materials. The permeable topsheet, substantially impermeable backsheet, absorbent core and other components of the absorbent articles in accordance with various implementations of the present invention may comprise various materials. Persons of ordinary skill in the art would be readily able to select appropriate materials for use in the various components of the present invention based upon the materials.

In accordance with various implementations of the present invention, the absorbent core may contain one or more fibers, one or more polymers or combinations thereof. Non-limiting exemplary fibers which may be used in the articles of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester by component fibers, surface modified polyester/polyester bicomponent fibers, cotton fibers or blends thereof. Preferably, cellulose acetate, rayon, Courtauld's LYOCEL, polyacrylonitrile, cotton fibers and cotton linters or combinations thereof are used in the present invention. More preferably, cellulose fibers are used as fiber material in the present invention.

Other materials may be added to fiber or pulp material which is optionally processed in a fiberizing apparatus, such as a hammermill. The additives may be added at any point in the process. Preferably, the additives are sprayed or injected into the airborne fibers prior to the depositing of the fibers on the forming surface 2. Non-limiting exemplary additives which may be incorporated into the process of the present invention include a polymer such as a super absorbent polymer (SAP), hydrophilic polymers, potato starch, corn starch, wheat starch or rice starch, or combinations thereof.

Various different combinations of materials may be used as are known to persons of ordinary skill in the art and which are described in U.S. Pat. No. 6,068,620 which is herein incorporated by reference. Preferably, the mixtures incorporated in the invention are substantially homogenous mixtures or uniformly distributed mixtures. Absorbent articles in accordance with an implementation of the present invention are prepared using conventional methods and materials well known to persons of ordinary skill in the art, using the guidelines provided herein.

The present invention further provides absorbent garments that include the absorbent article of the present invention. Non-limiting exemplary absorbent garments include diapers, adult incontinent products, feminine hygiene products, disposable sanitary products and the like. Non-limiting exemplary diapers include daytime diapers, nighttime diapers, daytime/nighttime diapers, long-term wear diapers, male diapers, female diapers, unisex diapers, travel diapers, medicated diapers, and the like.

According to an implementation of the invention, an absorbent garment is provided which comprises: a front and a rear waist portion cooperating to form a waist opening, each of the front and rear waist portion being defined by a skin-facing surface and a skin-opposing surface; a crotch region formed between said front waist portion and said rear waist portion; a pair of leg cutouts on opposed sides of the crotch region; and a pair of front wing regions on the front waist portion, each of the front wing regions defining the area of the front waist portion adjacent to each said leg cutout; a pair of back wing regions on the back waist portion, each of the back wing regions defining the area of the back waist portion adjacent to each said leg cutout; a friction-inducing substance disposed on the skin-facing surface at a friction-inducing substance application zone or plurality of friction-inducing substance application zones on the each of the front wing regions, said friction-inducing substance application zone or plurality of friction-inducing substance application zones being selectively placed to improve the fit of the absorbent garment on a wearer of said absorbent garment.

According to another implementation of the present invention, an absorbent garment comprises: a substantially impermeable backsheet; a permeable topsheet; an absorbent core disposed between the substantially impermeable backsheet and the skin-opposing surface of said permeable topsheet; a front and a rear waist portion cooperating to form a waist opening, each of the front and rear waist portion being defined on the skin-facing surface by the permeable topsheet and on the skin-opposing surface by the substantially impermeable backsheet; a crotch region formed between said front waist portion and said rear waist portion; a pair of leg cutouts on opposed sides of the crotch region; and a friction-inducing substance disposed on the skin-facing surface of the permeable topsheet at an application zone or plurality of application zones, said application zone or plurality of application zones being selectively placed to improve the fit of the absorbent garment on a wearer of said absorbent garment.

Also provided is a method for preparing the absorbent articles of the present invention. According to an implementation of the present invention, a method of preparing an absorbent article comprises: applying a friction-inducing substance to a permeable topsheet at an application zone or plurality of application zones, said application zone or plurality of application zones being selectively placed to improve the fit of the absorbent article on a wearer of said absorbent article; and forming the permeable topsheet into an absorbent article. Persons of ordinary skill in the art would be readily able to implement this process of the present invention using conventional materials and techniques, based upon the guidance provided herein.

In another implementation of the present invention, a method of preparing an absorbent article comprises: applying a friction-inducing substance or a pressure-sensitive adhesive to a permeable topsheet at an application zone or plurality of application zones, said application zone or plurality of application zones being selectively placed to hold each of two mechanical fasteners in a folded position during processing of said absorbent article; and forming the permeable topsheet into the absorbent article. As shown in FIG. 5, the mechanical fasteners are held in place by the friction-inducing substance during processing. Persons of ordinary skill in the art would be readily able to implement this process of the present invention using conventional materials and techniques, based upon the guidance provided herein.

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by those skilled in the art that other variations and modifications can easily be made within the scope of the invention as defined by the appended claims.

What is claimed is:

1. An absorbent article comprising:
a substantially impermeable backsheet;
a permeable topsheet;
an absorbent core disposed between the substantially impermeable backsheet and a skin-opposing surface of said permeable topsheet;
a friction-inducing substance adhered to both a skin-facing surface of the permeable topsheet at at least two application zones defined by a predetermined area adjacent to and approximately parallel to each of the two front-side application edges or each of the two back-side application edges and to a skin-opposing surface of the substantially impermeable backsheet at at least two application zones defined by a predetermined area adjacent to and approximately parallel to each of the two front-side application edges or each of the two back-side application edges; and
a pressure-sensitive adhesive disposed on a skin-facing surface of the permeable topsheet at two application zones, each said application zone being defined by a predetermined area adjacent to and approximately parallel to each of a pair of back-side application edges;
wherein said friction-inducing substance is a skin-friendly substance that increases the coefficient of friction between at least two opposing surfaces without adhering to the skin of the wearer.

2. The absorbent article of claim 1, wherein the friction-inducing substance is adhered to the skin-facing surface of the permeable topsheet at two application zones.

3. The absorbent article of claim 1, whereby the friction-inducing substance is engageable with the skin of a wearer of the absorbent article when in use.

4. The absorbent article of claim 1, wherein the friction-inducing substance increases the coefficient of friction between the skin-facing surface of the permeable topsheet and the skin of the wearer when the absorbent article is in use without adhering to the skin of the wearer.

5. The absorbent article of claim 1, wherein the friction-inducing substance increases the coefficient of friction between the permeable topsheet of the absorbent article and the skin of a wearer of the absorbent article by about 25% to about 500% when the absorbent article is in use.

6. The absorbent article of claim 1, wherein the friction-inducing substance increases the coefficient of friction between the permeable topsheet of the absorbent article and the skin of a wearer of the absorbent article by about 50% to about 200% when the absorbent article is in use.

7. The absorbent article of claim 1, wherein the friction-inducing substance increases the coefficient of friction between the permeable topsheet of the absorbent article and the skin of a wearer of the absorbent article by about 60% to about 140% when the absorbent article is in use.

8. The absorbent article of claim 1, wherein the friction-inducing substance increases the coefficient of friction between the permeable topsheet of the absorbent article and the skin of a wearer of the absorbent article by about 80% to about 100% when the absorbent article is in use.

9. The absorbent article of claim 1, wherein the friction-inducing substance is a skin-friendly substance.

10. The absorbent article of claim 1, wherein the friction-inducing substance is selected from the group consisting of rubber-solvents, cellulosics, gums, minerals, polymers, resins and combinations thereof.

11. The absorbent article of claim 1, wherein the friction-inducing substance is selected from the group consisting of polymers and combinations thereof.

12. The absorbent article of claim 1, wherein the friction-inducing substance is Product No. 10958-17-1 available from National Starch and Chemical, Inc. located in Bridgewater, N.J.

13. The absorbent article of claim 1, wherein the application zone forms a substantially rectangular area of about 2 mm to about 190 mm in width and about 5 mm to about 200 mm in length.

14. The absorbent article of claim 1, wherein said absorbent article is substantially evenly distributed around the body of the wearer during use.

15. An absorbent article comprising:
a substantially impermeable backsheet and a permeable topsheet; said substantially impermeable backsheet and said permeable topsheet being defined by a front edge, a back edge approximately parallel to said front edge, a pair of opposing front-side application edges and a pair of opposing back-side application edges, each of said front-side and back-side application edges being disposed between and approximately perpendicular to the front edge and the back edge, and a pair of opposing leg cutout edges disposed between the pair of front-side edges and the pair of back-side edges;
an absorbent core disposed between the substantially impermeable backsheet and a skin-opposing surface of said permeable topsheet;
a friction-inducing substance adhered to both a skin-facing surface of the permeable topsheet at at least two application zones defined by a predetermined area adjacent to and approximately parallel to each of the two front-side application edges or each of the two back-side application edges and to a skin-opposing surface of the substantially impermeable backsheet at at least two application zones defined by a predetermined area adjacent to and approximately parallel to each of the two front-side application edges or each of the two back-side application edges; and
a pressure-sensitive adhesive disposed on a skin-facing surface of the permeable topsheet at two application zones, each said application zone being defined by a predetermined area adjacent to and approximately parallel to each of a pair of back-side application edges;
wherein said friction-inducing substance is a skin-friendly substance that increases the coefficient of friction between at least two opposing surfaces without adhering to the skin of the wearer.

16. The absorbent article of claim 15, wherein the friction-inducing substance is adhered to the skin-facing surface of the permeable topsheet at two application zones, each said application zone being defined by a predetermined area adjacent to and approximately parallel to each of the two front-side application edges or each at the two back-side application edges.

17. The absorbent article of claim 15, wherein a friction-inducing substance is adhered to a skin-opposing surface of the substantially impermeable backsheet at two application zones, each said application zone being defined by a predetermined area adjacent to and approximately parallel to each of the two front-side application edges or each of the two back-side application edges.

18. The absorbent article of claim 17, wherein the friction-inducing substance is adhered to the skin-facing surface of the permeable topsheet at two application zones,
wherein the two application zones on the skin-facing surface of the permeable topsheet are defined by a predetermined area adjacent to and approximately parallel to each of the two front-side application edges; and
wherein the two application zones on the skin-facing surface of the permeable topsheet are defined by a predetermined area adjacent to and approximately parallel to each of the two front-side application edges or each of the two back-side application edges.

19. The absorbent article of claim 15, wherein an outmost portion of each application zone is about 0.1 mm to about 190 mm from said front-side application edge or said back-side application edge.

20. The absorbent article of claim 15, wherein an outmost portion of each application zone is about 5 mm to about 50 mm from said front-side application edge or said back-side application edge.

21. The absorbent article of claim 15, wherein a forward-most portion of each application zone adjacent to the front-side application edge is about 0 mm about 200 mm from the front edge of the permeable topsheet.

22. The absorbent article of claim 15, wherein a forward-most portion of each application zone adjacent to the front-side application edge is about 0 mm to about 100 mm from the front edge of the permeable topsheet.

23. The absorbent article of claim 15, whereby the friction-inducing substance is engageable with the skin of a wearer of the absorbent article when in use.

24. The absorbent article of claim 15, wherein the friction-inducing substance increases the coefficient of friction between the skin-facing surface of the permeable topsheet and the skin of the wearer when the absorbent article is in use without adhering to the skin of the wearer.

25. The absorbent article of claim 15, wherein the friction-inducing substance increases the coefficient of friction between the permeable topsheet of the absorbent article and the skin of a wearer of the absorbent article by about 25% to about 500% when the absorbent article is in use.

26. The absorbent article of claim 15, wherein the friction-inducing substance increases the coefficient of friction between the permeable topsheet of the absorbent article and the skin of a wearer of the absorbent article by about 50% to about 200% when the absorbent article is in use.

27. The absorbent article of claim 15, wherein the friction-inducing substance increases the coefficient of friction between the permeable topsheet of the absorbent article and the skin of a wearer of the absorbent article by about 60% to about 140% when the absorbent article is in use.

28. The absorbent article of claim 15, wherein the friction-inducing substance increases the coefficient of friction between the permeable topsheet of the absorbent article and the skin of a wearer of the absorbent article by about 80% to about 100% when the absorbent article is in use.

29. The absorbent article of claim 15, wherein the friction-inducing substance is a skin-friendly substance.

30. The absorbent article of claim 15, wherein the friction-inducing substance is selected from the group consisting of rubber-solvents, cellulosics, gums, minerals, polymers, resins.

31. The absorbent article of claim 15, wherein the friction-inducing substance is Product No. 10958-17-1 available from National Starch and Chemical. Inc. located in Bridgewater, N.J.

32. The absorbent article of claim 15, wherein the application zone forms a substantially rectangular area of about 2 mm to about 190 mm in width and about 5 mm to about 200 mm in length.

33. The absorbent article of claim 15, wherein said absorbent article is substantially evenly distributed around the body of the wearer during use.

34. The absorbent article of claim 15, wherein the application zone forms a substantially rectangular area of about 2 mm to about 190 mm in width and about 5 mm to about 200 mm in length.

35. The absorbent article of claim 15, wherein the application zone forms a substantially rectangular area of about 5 mm to about 60 mm in width and about 10 mm to about 100 mm in length.

36. The absorbent article of claim 15, wherein the friction-inducing substance covers the entire application zone.

37. The absorbent article of claim 15, wherein the friction-inducing substance partially covers the application zone.

38. The absorbent article of claim 15, wherein the friction-inducing substance partially covers the application zone.

39. The absorbent article of claim 38, wherein the friction-inducing substance forms a pattern thereon.

40. The absorbent article of claim 39, wherein the pattern is selected from the group consisting of spiral, random fiberization, zoned slot and combinations thereof.

41. The absorbent article of claim 39, wherein said pattern provides cost efficiency.

42. The absorbent article of claim 15, wherein said friction-inducing substance is of a substantially uniform application density.

43. The absorbent article of claim 15, further comprising a pressure-sensitive adhesive at a pressure-sensitive application zone or plurality of pressure-sensitive application zones, the pressure-sensitive adhesive zone or each of the plurality of pressure-sensitive application zones being of a predetermined area adjacent and parallel to the back application edges of the permeable topsheet.

44. The absorbent article of claim 43, wherein the pressure-sensitive adhesive is engageable with the skin-opposing surface of the substantially impermeable backsheet at a receiving zone.

45. An absorbent article comprising:
a substantially impermeable backsheet;
a permeable topsheet having a skin-facing surface and a skin-opposing surface; said permeable topsheet being defined by a front edge, a back edge approximately parallel to said front edge, two front-side application edges and two back-side application edges, each of said front-side and back-side application edges being approximately perpendicular to the front edge and the back edge, and two leg cutout edges disposed between the two front-side edges and the two back-side edges;
an absorbent core positioned between the substantially impermeable backsheet and the skin-opposing surface of said permeable topsheet;
a friction-inducing substance adhered to the skin-facing surface of said permeable topsheet at a pair of first application zones whereby the friction-inducing substance is engageable with the skin of a wearer of the absorbent article when in use, said first application zones being of a predetermined area adjacent and parallel to the front-side application edge, and to a skin-opposing surface of the substantially impermeable backsheet at at least two application zones defined by a predetermined area adjacent to and approximately parallel to each of the two front-side application edges or each of the two back-side application edges; and
a pressure-sensitive adhesive disposed on a skin-opposing surface of said substantially impermeable backsheet at a pair of second application zones, said second application zones being of a predetermined area adjacent and parallel to the back-side application edge;
wherein said friction-inducing substance is a skin-friendly substance that increases the coefficient of friction between at least two opposing surfaces without adhering to the skin of the wearer;
wherein said first application zones form a substantially rectangular area of about 2mm to about 190 mm in width and about 5 mm to about 200 mm in length; and
wherein an outmost portion of each of said first application zones is about 0.1 mm to about 190 mm from said front-side application edge or said back-side application edge.

46. The absorbent article of claim 45, wherein the friction-inducing substance increases the coefficient of friction between the skin-facing surface of the permeable topsheet and the skin-opposing surface of the substantially impermeable backsheet when the absorbent article is in use.

47. The absorbent article of claim 45, wherein the friction-inducing substance increases the coefficient of friction between the permeable topsheet of the absorbent article and the substantially impermeable backsheet of the absorbent article by about 25% to about 500% when the absorbent article is in use.

48. The absorbent article of claim 45, wherein the friction-inducing substance increases the coefficient of friction between the permeable topsheet of the absorbent article and the substantially impermeable backsheet of the absorbent article by about 50% to about 200% when the absorbent article is in use.

49. The absorbent article of claim 45, wherein the friction-inducing substance increases the coefficient of friction between the permeable topsheet of the absorbent article and the substantially impermeable backsheet of the absorbent article by about 60% to about 140% when the absorbent article is in use.

50. The absorbent article of claim 45, wherein the friction-inducing substance increases the coefficient of friction between the permeable topsheet of the absorbent article and the substantially impermeable backsheet of the absorbent article by about 80% to about 100% when the absorbent article is in use.

51. An absorbent garment, which comprises:
a front and a rear waist portion cooperating to form a waist opening, each of the front and rear waist portion being defined by a skin-facing surface and a skin-opposing surface;
a crotch region formed between said front waist portion and said rear waist portion;
a pair of leg cutouts on opposed sides of the crotch region; and
a pair of front wing regions on the front waist portion, each of the front wing regions defining an area of the front waist portion adjacent to each said leg cutout;
a pair of back wing regions on the back waist portion, each of the back wing regions defining an area of the back waist portion adjacent to each said leg cutout;
a friction-inducing substance adhered to both the skin-facing surface at a plurality of friction-inducing substance application zones on the each of the front wing regions and to the skin-opposing surface at at least two application zones defined by a predetermined area adjacent to and approximately parallel to each of the two front-side application edges or each of the two back-side application edges, said plurality of friction-inducing substance application zones being selectively placed to improve the fit of the absorbent garment on a wearer of said absorbent garment; and
a pressure-sensitive adhesive disposed on a skin-facing surface of the permeable topsheet at two application zones, each said application zone being defined by a predetermined area adjacent to and approximately parallel to each of a pair of back-side application edges;
wherein said friction-inducing substance is a skin-friendly substance that increases the coefficient of friction between at least two opposing surfaces without adhering to the skin of the wearer.

52. An absorbent garment, which comprises:
a substantially impermeable backsheet;
a permeable topsheet;
an absorbent core disposed between the substantially impermeable backsheet and a skin-opposing surface of said permeable topsheet;
a front and a rear waist portion cooperating to form a waist opening, each of the front and rear waist portion being defined on a skin-facing surface by the permeable topsheet and on a skin-opposing surface by the substantially impermeable backsheet;
a crotch region formed between said front waist portion and said rear waist portion;
a pair of leg cutouts on opposed sides of the crotch region; and
a friction-inducing substance adhered to both a skin-facing surface of the permeable topsheet at at least two application zones defined by predetermined area adjacent to and approximately parallel to each of the two front-side application edges or each of the two back-side application edges and to a skin-opposing surface of the substantially impermeable backsheet at at least two application zones defined by a predetermined area adjacent to and approximately parallel to each of the two front-side application edges or each of the two back-side application edges; and
a pressure-sensitive adhesive disposed on a skin-facing surface of the permeable topsheet at two application zones, each said application zone being defined by a predetermined area adjacent to and approximately parallel to each of a pair of back-side application edges;
wherein said friction-inducing substance is a skin-friendly substance that increases the coefficient of friction between at least two opposing surfaces without adhering to the skin of a wearer.

53. The absorbent garment of claim 52, further comprising a first leg gather and a second leg gather.

54. The absorbent garment of claim 52, wherein the absorbent garment is a diaper.

55. The absorbent garment of claim 52, wherein the absorbent garment is a unisex diaper.

56. The absorbent garment of claim 52, wherein the absorbent garment is a nighttime diaper.

57. The absorbent garment of claim 52, wherein the absorbent garment is a travel diaper.

58. The absorbent garment of claim 52, wherein the absorbent garment is an adult incontinent product.

59. A method of preparing an absorbent article comprising:
adhering a friction-inducing substance to both a skin-facing surface of a permeable topsheet at at least two application zones defined by a predetermined area adjacent to and approximately parallel to each of the two front-side application edges or each of the two back-side application edges and to a skin-opposing surface of the substantially impermeable backsheet at at least two application zones defined by a predetermined area adjacent to and approximately parallel to each of the two front-side application edges or each of the two back-side application edges, wherein said friction-inducing substance is a skin-friendly substance that increases the coefficient of friction between at least two opposing surfaces without adhering to at least one of said opposing surfaces;
adhering a pressure-sensitive adhesive to a skin-facing surface of the permeable topsheet at two application zones, each said application zone being defined by a predetermined area adjacent to and approximately parallel to each of a pair of back-side application edges; and
incorporating the permeable topsheet into an absorbent article.

60. A method of preparing an absorbent article comprising:
adhering a friction-inducing substance or a pressure sensitive adhesive to a permeable topsheet at an application zone or plurality of application zones, said application zone or plurality of application zones being selectively placed to hold each of two mechanical fasteners in a folded position during processing of said absorbent article, wherein said friction-inducing substance is a skin-friendly substance that increases the coefficient of friction between at least two opposing surfaces without adhering to at least one of said opposing surfaces;
adhering a friction-inducing substance to a skin-opposing surface of the substantially impermeable backsheet at at least two application zones defined by a predetermined area adjacent to and approximately parallel to each of the two front-side application edges or each of the two back-side application edges; and adhering a pressure-sensitive adhesive to a skin-facing surface of the permeable topsheet at two application zones, each said application zone being defined by a predetermined area adjacent to and approximately parallel to each of a pair of back-side application edges; and incorporating the permeable topsheet into the absorbent article.

* * * * *